US007447988B2

(12) United States Patent
Ross

(10) Patent No.: US 7,447,988 B2
(45) Date of Patent: Nov. 4, 2008

(54) AUGMENTATION SYSTEM FOR DOCUMENTATION

(76) Inventor: Gary E. Ross, 17200 Jeanette St., Southfield, MI (US) 48075

( * ) Notice: Subject to any disclaimer, the term of this patent is extended or adjusted under 35 U.S.C. 154(b) by 465 days.

(21) Appl. No.: 09/852,447

(22) Filed: May 9, 2001

(65) Prior Publication Data

US 2001/0042080 A1 Nov. 15, 2001

Related U.S. Application Data

(60) Provisional application No. 60/203,315, filed on May 10, 2000.

(51) Int. Cl.
*G06F 15/00* (2006.01)
*G06F 17/00* (2006.01)
(52) U.S. Cl. ............... 715/221; 715/222; 715/223; 715/224; 715/225; 715/226
(58) Field of Classification Search ............ 715/530, 715/531, 532
See application file for complete search history.

(56) References Cited

U.S. PATENT DOCUMENTS

| 4,914,590 | A | * | 4/1990 | Loatman et al. ............ 704/8 |
| 5,307,262 | A | * | 4/1994 | Ertel ...................... 705/2 |
| 5,483,443 | A | * | 1/1996 | Milstein et al. ........... 705/3 |
| 5,594,638 | A | * | 1/1997 | Iliff ..................... 705/3 |
| 5,660,176 | A | * | 8/1997 | Iliff ................... 600/300 |
| 5,737,539 | A | * | 4/1998 | Edelson et al. ............ 705/3 |
| 5,845,255 | A | * | 12/1998 | Mayaud .................. 705/3 |
| 5,870,768 | A | * | 2/1999 | Hekmatpour ........... 715/501.1 |
| 6,000,828 | A | * | 12/1999 | Leet ....................... 705/2 |
| 6,014,632 | A | * | 1/2000 | Gamble et al. ............ 705/4 |
| 6,449,627 | B1 | * | 9/2002 | Baer et al. .............. 715/514 |
| 6,529,876 | B1 | * | 3/2003 | Dart et al. ............... 705/4 |
| 6,611,840 | B1 | * | 8/2003 | Baer et al. ............. 707/102 |
| 6,839,701 | B1 | * | 1/2005 | Baer et al. ................ 707/3 |
| 2002/0002325 | A1 | * | 1/2002 | Iliff ................... 600/300 |
| 2002/0133460 | A1 | * | 9/2002 | Field .................... 705/40 |

OTHER PUBLICATIONS

McKeown, Kathleen R., et al., PERSIVAL, a system for personalized search and summarization over multimedia healthcare information, Jan. 2001, ACM Press, Proceedings of the 1st ACM/IEEE-CS joint conference on Digital libraries, pp. 331-340.*

* cited by examiner

*Primary Examiner*—Stephen Hong
*Assistant Examiner*—Nathan Hillery
(74) *Attorney, Agent, or Firm*—Kenneth I. Kohn; Kohn & Associates, PLLC

(57) ABSTRACT

According to the present invention, there is provided a documentation system including an augmenting mechanism that elicits more accurate conclusions through the analysis of entered information and predetermined criteria. The present invention also provides for a method of documentation based upon the augmenting mechanism and a method of augmenting to calculate more accurate conclusions based upon all entered information and related predetermined criteria. Additionally, the present invention includes a software program for operating the documentation system and method for the operation of the augmenting mechanism. The present invention provides for a computerized documentation entry system for determining more accurate conclusions including a software program having an augmenting mechanism and a graphic user interface for displaying, accessing and interacting with users of the documentation system. Preferably, the present invention is directed towards a system, software program, and method for accurately and completely determining payment reimbursement in the health care field.

1 Claim, 8 Drawing Sheets

Example of form that uses template prompted documentation.

Introductory comments after physician logs into the system.

Example of form that uses template prompted documentation.

Example of menu when physician requests to read the HCFA rules for the current form.

Software prompted HCFA rule when documentation is incomplete.

Summary of Encounter for Physician to use as a reference tool when submitting bill to third party payor.

Sample of E CPT4 Rules

| Encounter Type | CPT4 (E&M) | HPI | PFSH | ROS | Px | MDM DX | MDM data | MDM Risk |
|---|---|---|---|---|---|---|---|---|
| | 99*** | | A | | B | \multicolumn{2}{c}{any two of the above} C | |
| Outpatient New Visit | 201 | 1 | 0 | 0 | 1 | 0 | 0 | Minimal (Min) |
| Requires A B & C | 202 | 1 | 0 | 1 | 2 | 0 | 0 | Min |
| | 203 | 4 | 1 | 2 | 2 | 2 | 2 | Low |
| | 204 | 4 | 3 | 10 | 8 | 3 | 3 | Moderate (Mod) |
| | 205 | 4 | 3 | 10 | 8 | 4 | 4 | High |
| Outpatient Established Patient Visit | 211 | 0 | 0 | 0 | 0 | 1 | 0 | 0 |
| Requires any two of A B & C | 212 | 1 | 0 | 0 | 1 | 1 | 0 | Min |
| | 213 | 1 | 0 | 1 | 2 | 2 | 2 | Low |
| | 214 | 4 | 1 | 2 | 2 | 3 | 3 | Mod |
| | 215 | 4 | 2 | 10 | 8 | 4 | 4 | High |
| Inpatient H&P | 221 | 4 | 1 | 2 | 2 | 1 | 1 | Min |
| Requires A B & C | 222 | 4 | 3 | 10 | 8 | 3 | 3 | Mod |
| | 223 | 4 | 3 | 10 | 8 | 4 | 4 | High |
| Inpatient Established Patient Visit | 231 | 1 | 0 | 0 | 1 | 1 | 1 | Min |
| Requires any two of A B & C | 232 | 1 | 0 | 1 | 1 | 3 | 3 | Mod |
| | 233 | 4 | 1 | 2 | 2 | 4 | 4 | High |
| Inpatient Observation | 234 | 4 | 1 | 2 | 2 | 1 | 1 | Min |
| Requires A B & C | 235 | 4 | 3 | 10 | 8 | 3 | 3 | Mod |
| | 236 | 4 | 3 | 10 | 8 | 4 | 4 | High |
| Outpatient Consult | 241 | 1 | 0 | 0 | 1 | 1 | 0 | Min |
| Requires A B & C | 242 | 1 | 0 | 1 | 2 | 1 | 0 | Min |
| | 243 | 4 | 1 | 2 | 2 | 2 | 2 | Low |
| | 244 | 4 | 2 | 10 | 8 | 3 | 3 | Mod |
| | 245 | 4 | 2 | 10 | 8 | 4 | 4 | High |
| Inpatient Consult | 251 | 1 | 0 | 0 | 1 | 1 | 1 | Min |
| Requires A B & C | 252 | 1 | 0 | 1 | 2 | 1 | 1 | Min |
| | 253 | 4 | 1 | 2 | 2 | 2 | 2 | Low |
| | 254 | 4 | 3 | 10 | 8 | 3 | 3 | Mod |
| | 255 | 4 | 3 | 10 | 8 | 4 | 4 | High |
| Emergency Department | 281 | 1 | 0 | 0 | 1 | 1 | 0 | Min |
| Requires A B & C | 282 | 1 | 0 | 1 | 2 | 2 | 2 | Low |
| | 283 | 4 | 0 | 1 | 2 | 3 | 3 | Mod |
| | 284 | 4 | 1 | 2 | 2 | 3 | 3 | Mod |
| | 285 | 4 | 2 | 10 | 8 | 4 | 4 | High |
| ECF H&P | 301 | 4 | 1 | 2 | 8 | 2 | 2 | Low |
| Requires A B & C | 302 | 4 | 1 | 2 | 8 | 3 | 3 | Mod |
| | 303 | 4 | 3 | 10 | 8 | 4 | 4 | High |
| ECF Established Patient Visit | 311 | 1 | 0 | 0 | 1 | 1 | 0 | Low |
| Requires A B & C | 312 | 1 | 0 | 1 | 2 | 3 | 3 | Mod |
| | 313 | 4 | 1 | 2 | 2 | 3 | 3 | High |

E&M-CPT Reimbure.xls

FIGURE 8

AUGMENTATION SYSTEM FOR DOCUMENTATION

CROSSREFERENCE TO RELATED APPLICATIONS

This application claims the benefit of priority under 35 U.S.C. Section 119(e) of U.S. Provisional Patent Application No. 60/203,315, filed May 10, 2000, which is incorporated herein by reference.

BACKGROUND OF THE INVENTION

1. Field of the Invention

This invention generally relates to the field of computer-based documentation systems. Specifically, the invention relates to systems used for medical documentation of medical records and recovery of payments. Additionally, the invention is used in non-medical areas, such as automotive repair, legal services, and other service oriented businesses where records are kept as criteria for goals such as compensation.

2. Description of Related Art

Current documentation systems exist in all areas of businesses and services. These documentation systems have been improved through digital methods and the implementation of computers. There are however, numerous problems arising with documentation systems that include, but are not limited to legibility, clarity, completeness, and accuracy of documenting data.

Particularly in the medical field, clear, accurate, and complete documentation of patient encounters with health care providers is crucial for proper patient care and payment reimbursement by third party payers. In fact, improper patient care occurs due to the inability of health care providers to read unclear and incomplete documented notes. Frequently, medical histories, physical findings, diagnosis and subsequent treatment are lacking in detail within the documentation of the patient's encounter with the health care provider. Additionally, the true severity of the patient's illness is not accurately reflected in the documentation of the patient's encounter. Thus, incomplete diagnosis, which leads to misleading treatment and improper reimbursement, occurs.

In addition to problems with patient care, payment reimbursement based on medical codes and documentation is incomplete and not properly provided. The documentation of the patient encounters must be done in a proper format and include certain criteria. The criteria or information regarding the patient encounter must accurately describe the medical history, diagnosis, assessment of problems, and treatment performed on the patient. Many times, the criteria or information entered regarding the patient encounter are misleading or incomplete for medical coding. As a result, satisfying government and insurance regulations is very difficult and receiving the appropriate level of payment does not occur.

The current medical reimbursement payment system utilizes physician Evaluation and Management CPT-4 Codes (E&M CPT-4 Codes) that relate to physician and hospital revenue. Third party payers, such as the Health Care Finance Administration (HCFA) who oversees the Medicare program, are responsible for payment reimbursement. Hospitals and other health care providers are under government scrutiny because of the known inaccuracies and potential fraud occurring in assigning E&M CPT-4 Codes in relation to the services rendered by health care providers. E&M CPT-4 Codes are assigned and correlate to the medical treatment and service rendered to the patient by the health care provider. Assignment of the E&M CPT-4 Codes directly depends upon the documentation made by the health care provider. The E&M CPT-4 Codes are used for defining the reimbursement levels for the health care provider's services.

The terminology and detail of documentation for certain diagnoses are frequently incomplete with regard to the requirements for proper payment reimbursement. In order to receive the appropriate level of payment reimbursement, the proper medical billing codes must be assigned to the services rendered by the health care provider. In turn, proper medical billing codes will determine the level of reimbursement. The description of the appropriate services rendered is crucial in ultimately determining payment reimbursement. Therefore, accurate and complete documentation of the patient encounter must meet certain criteria in order to be assigned to the appropriate medical billing code.

Third party payers, such as HCFA, use a classification method known as Diagnosis Related Groups (DRG) to reimburse hospitals for inpatient care. The classifications are defined by the patient's diagnoses and procedures performed on them. Each DRG classification assigns a fixed, resource consumption to a particular illness as measured by the length of stay and cost.

Most third party payers have adopted criteria for admitting patients to an acute care hospital as well as for indicating which patients should undergo certain procedures. Frequently, documentation by the physician does not address all the details of the history and physical for a particular patient; therefore, key elements are missing that would otherwise support the need for a patient to be admitted or to undergo the procedure. Therefore, reimbursement rates are not appropriate, or an actual denial occurs from the third party payer.

Although current systems exist to aid medical documentation, there is a need for improvement. Current systems used in other fields have greatly improved documentation. There are many programs and applications existing that assist the individual in documenting information by providing prompting functions. For instance, the Turbo Tax program has a prompting feature that asks questions based on previous questions. Therefore, answering questions in one manner leads to another question that will elicit more detailed information. In the Turbo Tax program, the first question asks whether or not the individual has W-2 income. If the individual answers "yes," the program asks the individual to then provide pertinent data for a W-2. There are other programs such as Microsoft Excel that utilize formulas that prompt the user with a message if the user makes a mistake with the formula. The software prompts the user with the option to view the location of the mistake. If the user chooses to view the mistake, help comes up on the screen with the information to correct the error.

In the medical field, the medical documentation systems currently on the market are directed to outpatient documentation only. Some systems are geared toward extended care facilities and others toward creating complete electronic medical records. There are no systems that possess a processing mechanism that assists in the completing of patient records to augment the medical coding in both the outpatient and inpatient settings.

Accordingly, in response to the documentation systems currently existing, there is a need for a system that provides more complete, accurate, accessible and legible documentation of the health care provider component of the medical record. Further, there is a need for a system that elicits more accurate conclusions through the analysis of entered information and predetermined criteria input. Finally, there is a need for a system to augment the medical coding in the inpatient setting to obtain accurate DRG-based reimbursement.

SUMMARY OF THE INVENTION

According to the present invention, there is provided a documentation system including an augmenting mechanism that elicits more accurate conclusions through the analysis of entered information and predetermined criteria. The present invention also provides for a method of documentation based upon the augmenting mechanism and a method of augmentation to calculate more accurate conclusions based upon all entered information and related predetermined criteria. Additionally, the present invention includes a software program for operating the documentation system and method for the operation of the augmenting mechanism. The present invention provides for a computerized documentation entry system for determining more accurate conclusions including a software program having an augmenting mechanism and a graphic user interface for displaying, accessing and interacting with users of the documentation system. Preferably, the present invention is directed towards a system, software program, and method for accurately and completely determining payment reimbursement in the health care field.

DESCRIPTION OF THE DRAWINGS

Other advantages of the present invention will be readily appreciated, as the same becomes better understood by reference to the following detailed description when considered in connection with the accompanying drawings wherein:

FIG. 8 is a chart illustrating various levels of payment reimbursement under different E&M CPT-4 Codes.

DETAILED DESCRIPTION OF THE INVENTION

Figure 1:
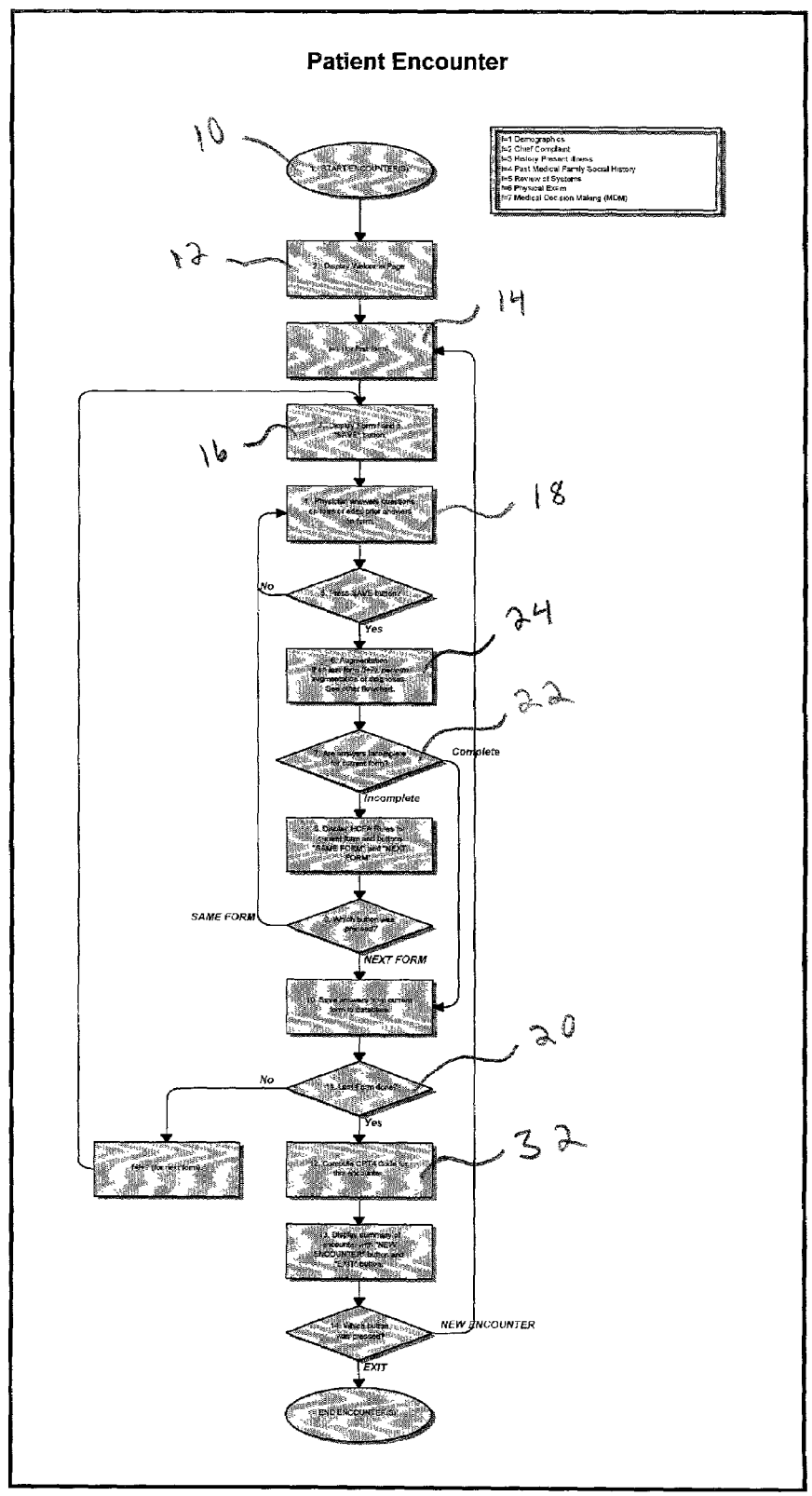
FIG. 1 is a flow chart diagram illustrating a preferred method of the present invention used during a patient encounter with a health care provider.

Generally, the present invention provides a system and method for the documentation of information. The present invention includes an augmenting mechanism that elicits more accurate conclusions through the analysis of entered information and inputted predetermined criteria. In the preferred embodiment, the present invention is directed towards improved documentation of patient encounters with health care providers. Specifically, the present invention is a documentation system and method for augmenting entered information by eliciting more accurate conclusions through the analysis of the entered information and related predetermined criteria. The information is displayed for interaction with the health care provider who has the opportunity to agree or disagree with the augmented conclusions.

The term "code(s)" as used herein is meant to include, but is not limited to, medical codes, payment codes, billing codes, accounting codes, and any other similar codes used relating to payment, reimbursement, debt, and costs.

The term "E&M CPT-4 Codes," "CPT," and "CPT-4 Codes" as used herein are meant to include, but are not limited to, current medical reimbursement payment system relating to reimbursement of physicians and hospitals for treatment and services rendered to a patient. Assignment of these codes directly depends upon the documentation made by the health care provider and are used for defining the reimbursement levels for the health care provider's services. The Health Care Financing Administration (HCFA) Common Procedure Coding System (HCPCS) describes physician services. Level 1 codes are known as CPT codes and are established by the American Medical Association (AMA). Physicians' Current Procedural Terminology is the source that describes the procedural and medical service components of physician services. CPT is a standardized system of five-digit codes and descriptive terms used to report medical services and procedures performed by physicians. Working together with the ICD-9 coding methodology (defined below), the CPT code is submitted to third party payers for reimbursement.

The term "ICD-9 Codes" as used herein is meant to include, but is not limited to, the International Classification of Diseases, *Clinical Modification*, Ninth revision. The *Clinical Modification* is the single source for diagnostic coding in the United States. ICD-9 Codes translate written terminology or descriptions into universal numeric or alphanumeric codes. Relative to reimbursement, diagnostic codes serve to establish medical necessity, without which, third party payers will not reimburse.

The terms "APGs" or "APCs" as used herein are meant to include, but are not limited to, refer to a reimbursement methodology for outpatient technical services provided by a medical provider. This methodology is recognized by third party payers, such as HCFA.

The term "DRGs" as used herein is meant to include, but is not limited to, the method HCFA uses to reimburse hospitals. It is a classification method whose patient types are defined by patient's diagnoses and/or procedures. Each DRG classification assigns a fixed resource consumption to a particular illness as measured by hospital length of stay and cost.

The terms "Health Care Finance Administration," and "HCFA" as used herein are meant to include, but are not limited to, a third party payer or administration that monitors and distributes payments under the Medicare system.

The term "Medical Coder" as used herein is meant to include, but is not limited to, a professional who translates documented written diagnoses and procedures into numeric and alphanumeric codes. Examples of codes include ICD-9 and CPT codes.

The term "conclusions" as used herein is meant to include, but is not limited to, codes, information, data, diagnosis, treatment, and any other similar desired outcome. Usually, such conclusions are based upon an inspection followed by an analysis. For example, a doctor examines a patient and based upon the examination or "criteria," a diagnosis is reached, the diagnosis herein being a conclusion.

The term "criteria" as used herein is meant to include, but is not limited to, phrases, words, medication, formulas, numbers, symbols, and any other similar symbols that are the basis for the various conclusions. The criteria are, for example, signs or symptoms noted by a physician during an examination. In accordance with the present invention, as discussed in detail below, previously discovered criteria can also be used to derive the conclusions. Such criteria are a basis for payment.

The term "information prompting form" as used herein is meant to include, but is not limited to, a form containing queries requiring responses that are related to conclusions. The form provides the user with a selection of answer choices or allows the user to freely enter text responses to the queries.

The terms "data" and "information" as used herein means any answer responding to a prompted or elicited query. The answer includes, but is not limited to, demographic information, personal patient information, identification, symptoms, descriptions, and any words describing or responding to the prompted or elicited query.

The terms "regulations" and "rules" as used herein are meant to include, but are not limited to, the HCFA rules, government regulations, standardized regulations, and any other similar rules. Usually, the rules determine the criteria and conclusions necessary to gain a goal. For example, certain symptoms must be noted to form a basis for a diagnosis to obtain payment under HCFA rules.

The term "prompting" as used herein is meant to include, but is not limited to, eliciting, requesting and suggesting responses to any query related to obtaining a desired conclusion. Preferably, prompting is done on a computer screen through a drop down menu list.

The term "augmenting" as used herein is meant to include, but is not limited to, adding, deleting, modifying, and altering entered data or information. Augmenting is achieved in response to a prompting, wherein the user notes additions or substitutions to the criteria and/or conclusions and makes adjustments accordingly.

The term "individual" as used herein is meant to include, but is not limited to, a person, patient, customer, client and any other similar person whom the information and data being entered is concerning.

The term "users" as used herein is meant to include, but is not limited to, health care providers, lawyers, accountants, repair personnel, and any other similar individuals who utilize the system and method disclosed herein.

The term "settings" as used herein is meant to include, but is not limited to, hospitals, business offices, garages, service stations, emergency rooms, medical offices, nursing facilities, extended care facilities, and any other similar business settings in which the present invention is utilized.

The term "health care provider(s)" as used herein is meant to include, but is not limited to, physicians, residents, attending physician, fellow, student, physician assistants, nurses, nurse's aides, and any other similar health care personnel responsible for the entry of patient's medical history, treatment and diagnosis thereof.

The terms "encounter" and "patient encounter" as used herein are meant to include, but are not limited to, any interaction between a service provider and an individual requiring the service. For example, an encounter is between a physician and patient or between a repair mechanic and automobile owner.

The term "demographics" as used herein is meant to include, but is not limited to, personal identification information, address, phone numbers, personal contacts, age, insurance information, and other similar descriptive information relevant to the encounter.

The term "chief complaint(s)" as used herein is meant to include, but is not limited to, any physical, mental, and emotional reasons requiring any service or aid thereof.

The term "history of present illness" as used herein is meant to include, but is not limited to, a chronological description of the development of the patient's illness from the first sign or symptom to the present signs or symptoms. It usually encompasses eight elements: location, quality, severity, duration, timing, context, modifying factors, and associated signs or symptoms.

The term "Past Medical Family Social History" as used herein is meant to include, but is not limited to, a description of the patient's past medical and surgical history, family history and social history. Past medical history is a review of the patient's past experiences with illnesses, procedures, injuries, and treatments that include, but are not limited to, information about prior major illnesses and injuries, prior surgical procedures, prior hospitalizations, medications, allergies, age appropriate immunization status, and age appropriate feeding and dietary status. Family history is a review of medical events occurring in the patient's family, which include hereditary diseases or diseases placing the patient at risk. Relevant family history include, but are not limited to, information about the health status or cause of death of immediate family members, specific diseases relate to problems noted in the chief complaint, or history of present illness or review of systems. Social history is an age appropriate review of activities including, but not limited to, information about marital status, living arrangements, employment or occupational history, use of drugs, alcohol, use of tobacco, level of education and sexual history.

The term "Review of Systems" as used herein is meant to include, but is not limited to, an inventory of body systems obtained through a series of questions seeking to identify signs or symptoms that the patient has that is related to the reason for the encounter. It usually encompasses the following systems: Constitutional, eyes, ears/nose/mouth/throat, cardiovascular, respiratory, gastrointestinal, genital/urinary, musculoskeletal, neurological, psychiatric, endocrine, integumentary, hematologic and lymphatic, and allergic or immunologic.

The term "Physical Exam" as used herein is meant to include, but is not limited to, the physical examination of the patient or individual.

The term "Medical Decision Making" as used herein is meant to include, but is not limited to, the number of possible diagnoses or management options, the amount or complexity of medical records, diagnostic tests of other information that is reviewed and analyzed, the risk of complications morbidity or mortality, and co-morbidity associated with the patient's reason for the encounter. Also included are the diagnostic procedures or management options.

The terms "Data" and "Risk" when used in relation to medical decision making are meant to include, but are not limited to, data referring to information reviewed on the types of diagnostic tests ordered or obtained, a decision to obtain and review old medical records, and history obtained from sources other than the patient. Risk refers to the likelihood of significant complications, morbidity, mortality associated with the patient's presenting problems, and the diagnostic procedures or the possible management options.

The present invention is utilized for numerous reasons and in numerous settings. The present invention relates to various processes that include, but are not limited to, documentation, filing, billing, accounting, and any other similar process that elicits the recitation and documentation of information related to predetermined criteria input. Preferably though, the present invention is well suited for use with payment reimbursement systems with regard to medical treatment and services.

The present invention is utilized in numerous settings and fields. Although the preferred embodiment of the present invention is for use in the health care field, the present invention is operable in fields including, but not limited to, law, engineering, accounting, businesses and any other fields needing a documentation system and method as described herein. In particular, the present invention is well suited for use in fields that require conducting client or customer interviews and subsequent documentation of the encounter incurred therein. Therefore, the present invention is usable in areas further including, but not limited to, specific specialty areas of medicine, service-oriented business such as automotive repair services, and any other similar client or customer related businesses.

The present invention generally operates through the use of information prompting forms that are specifically tailored towards desired areas of businesses or specialties. Because the present invention is fully adaptable for augmenting and documenting specific information desired by the user, it provides specific augmenting functions relating to any medical specialty such as cardiology, internal medicine, orthopedics and family practice. Moreover, the present invention is fully expandable for use in settings requiring enormous data collection and documentation including, but not limited to, hospitals, medical offices, business offices, service centers, and any other similar business settings.

The present invention is accessible through any device possessing the appropriate hardware capable of operating the system of the present invention. Appropriate devices include, but are not limited to, hand-held devices, portable computers, desktop computers, wireless devices, web-based technology systems, touch screen devices, typing devices, and any other similar electronic device that allows the entry of information known to those of skill in the art. Entry of information occurs through input devices including, but not limited to, keyboards, electronic pens, mouse devices, voice activation devices, bar code scanners, and any other similar electronic input devices known to those of skill in the art.

The present invention works on a single device and also works in unison with other networked devices. Thus, wired or wireless transmission from the device to a common server is possible. The data is stored on the device itself, the server, common server via the Internet, or central data warehouse outside of a facility. The present invention allows for simultaneous, multiple users.

Other functions and aspects of the documentation system of the present invention include, but are not limited to, mechanisms for free text entries by the user, data accuracy checking mechanisms, data storage mechanisms that record predetermined criteria, entered information, and conclusions, and security mechanisms that restrict access to the system of the present invention. The security mechanism generally requires the user to provide a user name and password. Additionally, the present invention features a checking mechanism that checks the completeness of all data and information entered into the system. Finally, one feature of the present invention is the presence of various links or options that are selected by the user to access various information regarding the individual who is involved with the encounter, information relating to the predetermined criteria, and previously entered information part of the electronic records.

The present invention includes a software program encoding for all of the functions of the documentation system, documentation method, and specifically for the augmenting mechanism to elicit more accurate conclusions through the analysis of entered information and predetermined criteria input. Thus, the software program encodes for functions including, but not limited to, data addition and substituting mechanisms, elicitation data base, accuracy confirming mechanisms, security mechanisms for restricting access to the software, searching mechanisms, linking mechanisms for linking to a listing and description of predetermined criteria, data storage mechanisms, and a free-text entry mechanism.

The software program is accessible through communication systems including, but not limited to, the Internet, Intranet, Extranet, and any other similar electronic mechanism known to those of skill in the art. Additionally, the software is capable of being interfaced with currently existing software programs and facility registration programs using such interfaces as HL7 or XML.

The augmenting mechanism of the present invention is a critical function used to provide the user with the ability to intelligently and accurately set forth criteria and conclusions to reach a goal therewith. The augmenting mechanism is a selection option mechanism that further includes mechanisms for adding and substituting related information. The augmenting mechanism also includes an elicitation database for intelligently suggesting more accurate conclusions, alternative conclusions, and predetermined criteria to support the conclusions. For instance, in the health care field, the augmentation of criteria, such as symptoms, and conclusions, such as diagnosis, assures the user of accurately setting forth a basis in accord with rules governing payment for services.

The augmenting mechanism is a selection option mechanism that assists the user in providing more complete and accurate conclusions. The augmenting mechanism is adapted to analyze any kind of criteria. The criteria include, but are not limited to, various words, phrases, and numbers. The criteria provide a basis for the conclusions the system is more accurately determining. In providing more accurate conclusions, the augmenting mechanism prompts the user to enter more detailed data or conclusions. The conclusions are formulated from predetermined criteria that have been entered into the system of the present invention.

The present invention further includes a documentation system comprising a processor; a graphic user interface including a display mechanism connected to the processor and input mechanism for communicating with the processor; data memory storage mechanism; and the software described herein.

In operation, the documentation system involves a method including the steps of: inputting predetermined criteria into a documentation system comprising information prompting forms; selecting a desired information prompting form; inputting data into the information prompting form; modifying the inputted data to provide more accurate conclusions based upon the predetermined criteria; and calculating more accurate conclusions based upon at least one completely entered information prompting form and all related predetermined criteria.

The documentation method generally includes navigating through various information prompting forms containing queries relevant to an encounter. Initially, the user interacts with a main menu page before continuing through the various information prompting forms. The information prompting forms are either blank or contain previously entered information. An important feature to documentation method is the augmenting step of eliciting more accurate conclusions based on entered information and predetermined criteria. The augmenting step also adds, deletes and modifies inputted data relating to the predetermined criteria. Furthermore, the augmenting step verifies the accuracy and completeness of information inputted into the information prompting form and provides a listing and description of predetermined criteria. Another step of the documentation method includes, but is not limited to, the calculating step including a saving step for recording inputted information and calculated conclusions and summarizing step for providing a summary of all entered information.

In operation, the augmenting mechanism involves a method comprising the steps of: displaying previously entered information and corresponding conclusions; selecting the desired information and corresponding conclusions to be augmented; providing at least one of alternative conclusions and additional criteria to be inputted; choosing at least one of the previously entered information, corresponding conclusions, alternative conclusions, and additional criteria; and calculating more accurate conclusions based upon all entered information and related predetermined criteria.

The augmentation method further includes displaying a selection of prompted information forms; providing more accurate and alternative conclusions, and predetermined criteria supporting the conclusions; and choosing, adding, deleting, or modifying a conclusion. Additionally, the augmentation method includes providing additionally prompted information forms.

Although there are numerous embodiments of the present invention, the preferred embodiment is directed towards improved documentation of patient encounters with health care providers. Patient encounters with health care providers, particularly physicians, require documentation of various data regarding the patient, illness, symptoms and problems. Generally, a patient encounter (FIG. 1) is any type of interaction between a patient and a health care provider occurring during a routine appointment, emergency room visit, surgical procedure or any other similar occurrence wherein a service is provided to the patient by the health care provider. The information entered includes, but is not limited to patient history, personal and demographic information such as the patient's name, address, phone number, age, sex, insurance information, and other information relevant to the patient encounter.

The preferred embodiment of the present invention is directed towards improved documentation of patient encounters with health care providers. Specifically, the present invention is a documentation system and method for eliciting more accurate conclusions, such as diagnosis and medical billing codes, through the analysis of previously entered data and predetermined criteria. Thus, the present invention assists the health care provider to more accurately document patient information, diagnosis, treatment, and services in order to enhance patient care as well as to allow the health care provider to be fully and properly reimbursed from third party payers. Moreover, the use of the present invention allows for the migration of lower weighted DRGs to higher weighted DRGs when appropriate. The use of the present invention enhances the compliance function for both physicians and hospitals and ultimately minimizes the risk of violating HCFA and other third party payer regulations.

The preferred embodiment is based on a documentation system that is operable and accessible through computer based systems. The system is in communication with a network server and database containing previously entered information about patients. The health care provider has access to any previously entered information through the networked computer or in the alternative, has the ability to add new information and new files regarding new patients.

In addition to providing a mechanism for entering and documenting data regarding a patient, the present invention aids in providing more accurate conclusions or billing codes in relation to the entered information and predetermined criteria. The present invention interacts with the health care provider by prompting the elicitation of more detailed documentation, data or information regarding the patient encounter. Additionally, the present invention elicits from the health care provider more accurate conclusions, alternative conclusions, or additional conclusions. In the preferred embodiment, the conclusions are medical billing codes or diagnoses, or additional information or documentation.

Figure 3:
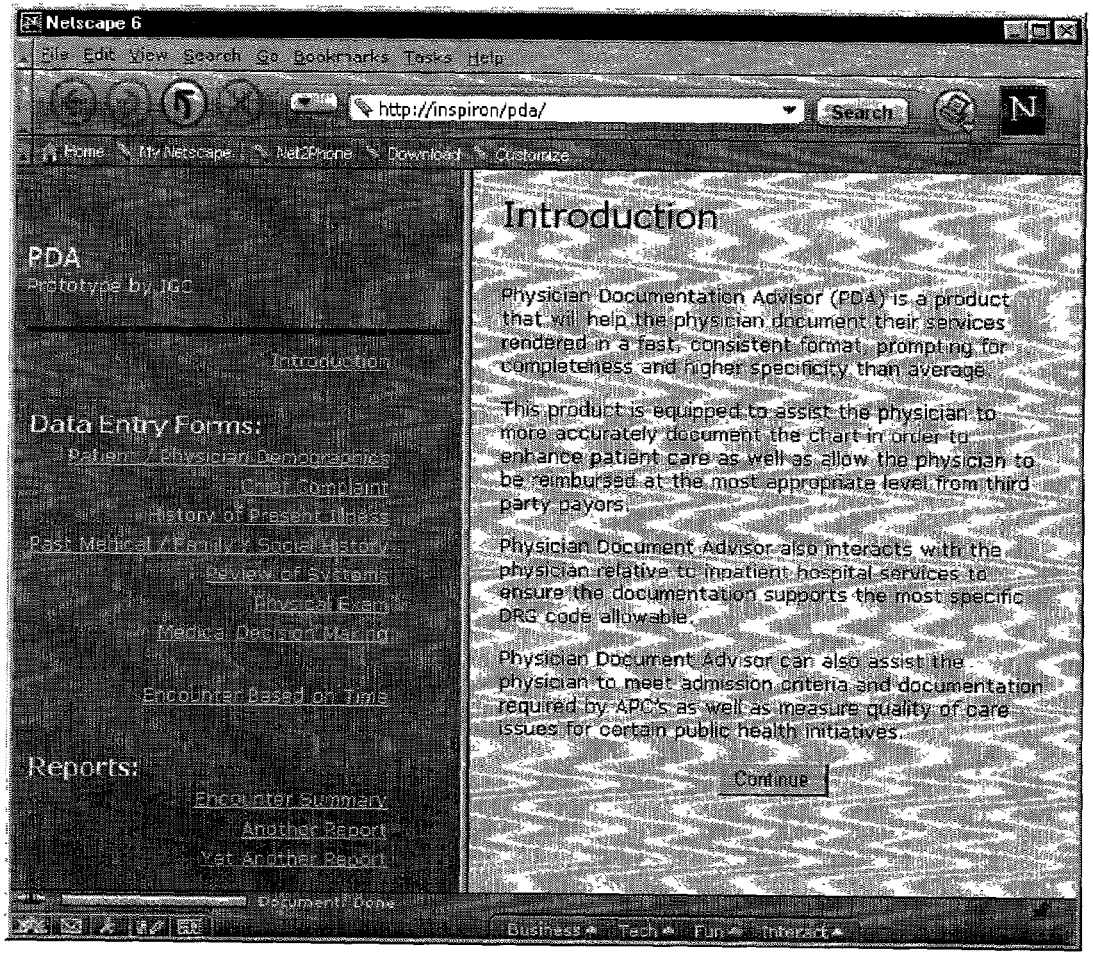
FIG. 3 is a view of one embodiment of the present invention on a web-based browser, this figure being an opening page or main menu display seen by a user after logging into the system of the present invention.

In the preferred embodiment, the health care provider must log into the system by providing a user name and password in order to gain access to all confidential patient informational files. Once access to the documentation system is allowed, the user accesses a main menu page (12) wherein the health care provider selects the patient file to be accessed or enters new patient information. Each patient file contains different information prompting forms (14) from which the user then selects to view. The user selects the desired form through drop down menus or links viewed on the main menu page. (FIG. 3) If the user desires to perform an auto completion search utilizing the present invention's data entry mechanism, then the user simply types in abbreviated or completed terms to be searched into the appropriate space.

Information documented with the system of the preferred embodiment includes, but is not limited to, site of documentation consistent with HCFA requirements ("in-hospital," "outpatient," "home visit" or "skilled nursing home"); type of documentation ("history and physical," "consult" or "repeat visit"); and medical specialty (Cardiology, Neurology, Pulmonary or Surgery) Within each general category of information, custom menus with more specific information is provided. The general categories are consistent with HCFA requirements. Information is entered through typing, writing, or pull-down menus. The health care provider enters the appropriate documentation within each drop-down menu to be saved as part of the final document. The drop-down menus are customized for each facility and even for an individual physician.

Figure 4:
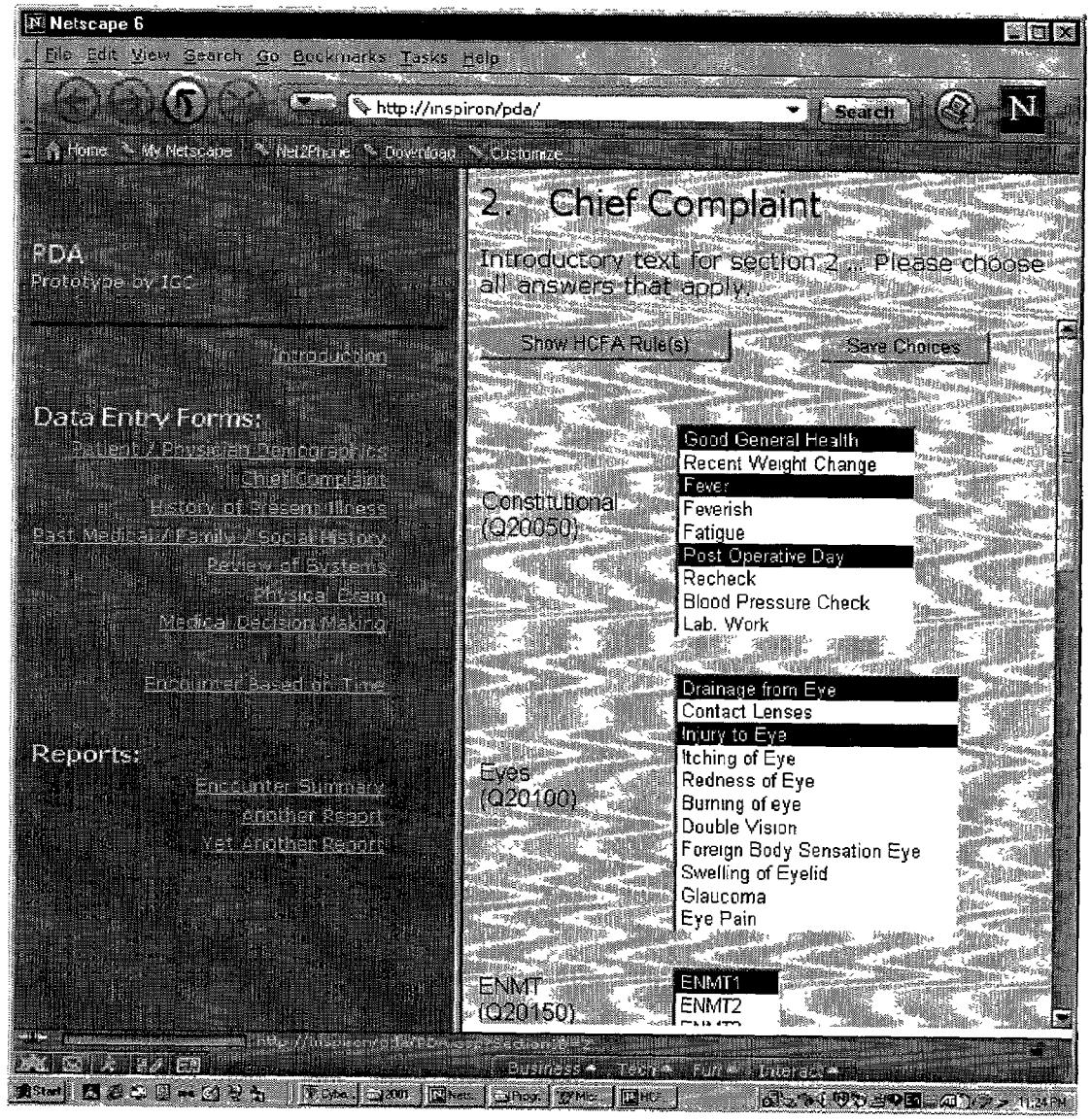
FIG. 4 is a view of one embodiment of the present invention on the web-based browser, this figure illustrating an example of an information prompting form that elicits information related to predetermined criteria input.
Figure 5:
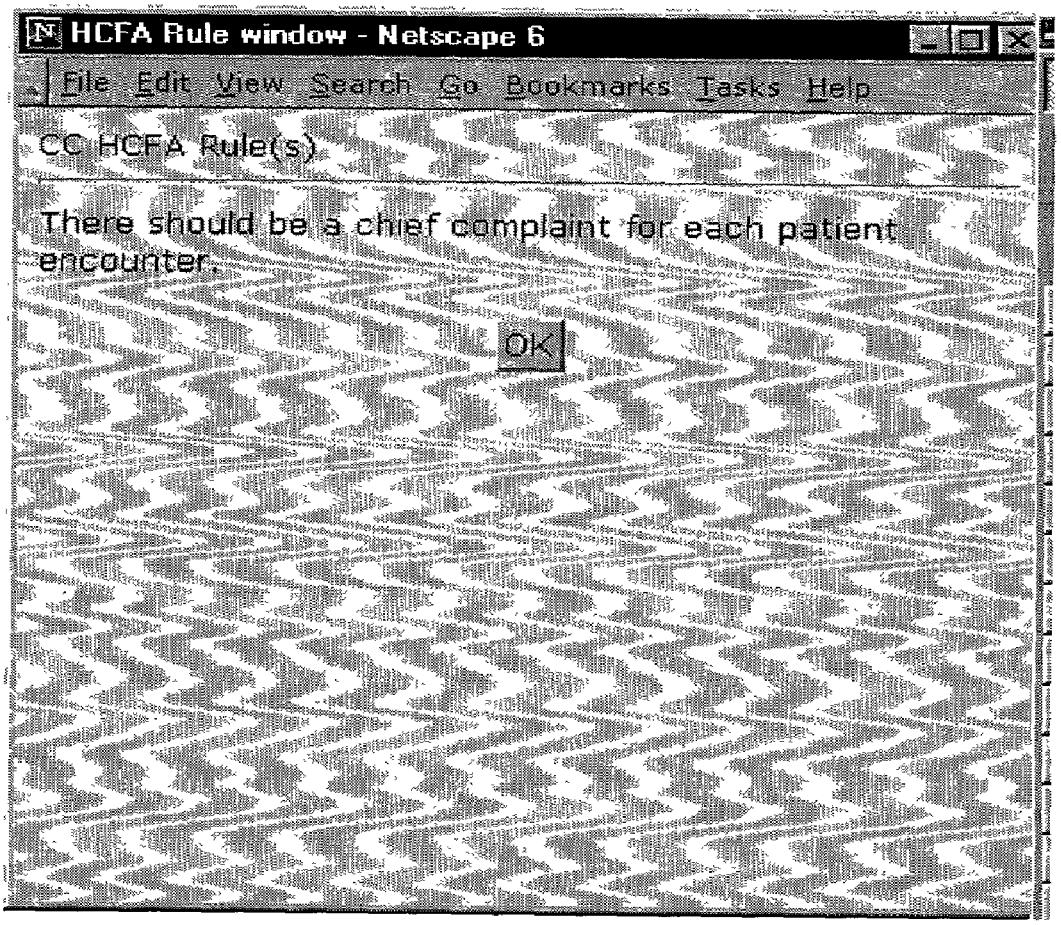
FIG. 5 is a view of one embodiment of the present invention on a web-based browser, this figure illustrating an example of information displayed regarding the predetermined criteria input that is accessible through the preferred embodiment of the present invention, in this case, the predetermined criteria being the HCFA rules.
Figure 6:
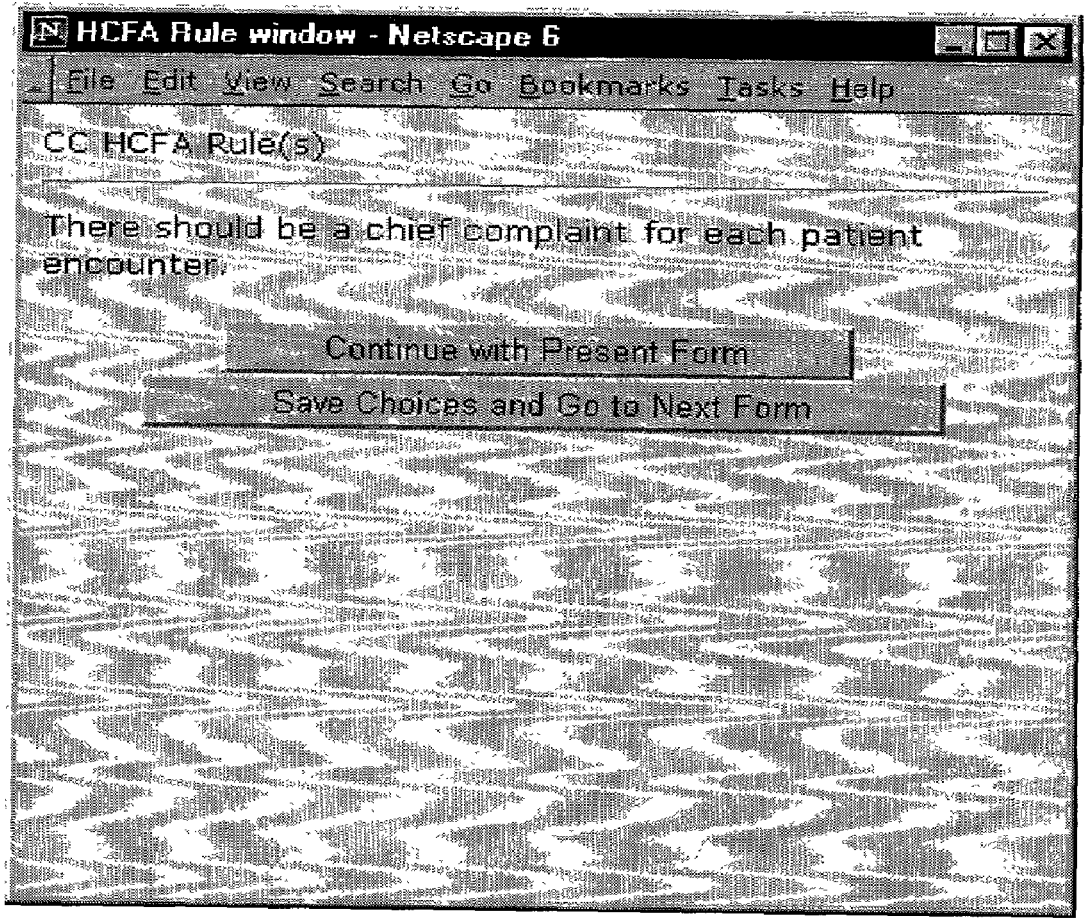
FIG. 6 is a view of one embodiment of the present invention on a web-based browser, this figure illustrating a prompting feature of the present invention that allows the user to access currently used forms and to continue with a selected form.

Each information prompting form contains different prompts that query the health care provider to supply data or information regarding the patient encounters. The forms include, but are not limited to forms for eliciting information regarding demographics, chief complaints (FIG. 4), history of present illness, past medical family social history, review of systems, and results of a physical exam. These forms elicit from the health care provider the appropriate criteria needed to determine the appropriate medical billing code. The medical billing codes in turn determine payment reimbursement to the health care provider. In the preferred embodiment, the prompts present on each form have predetermined answers or allow for free-text entry of answers appropriate to each prompted query. Additionally, the forms allow the user to type in appropriate remarks and notes.

Figure 2:
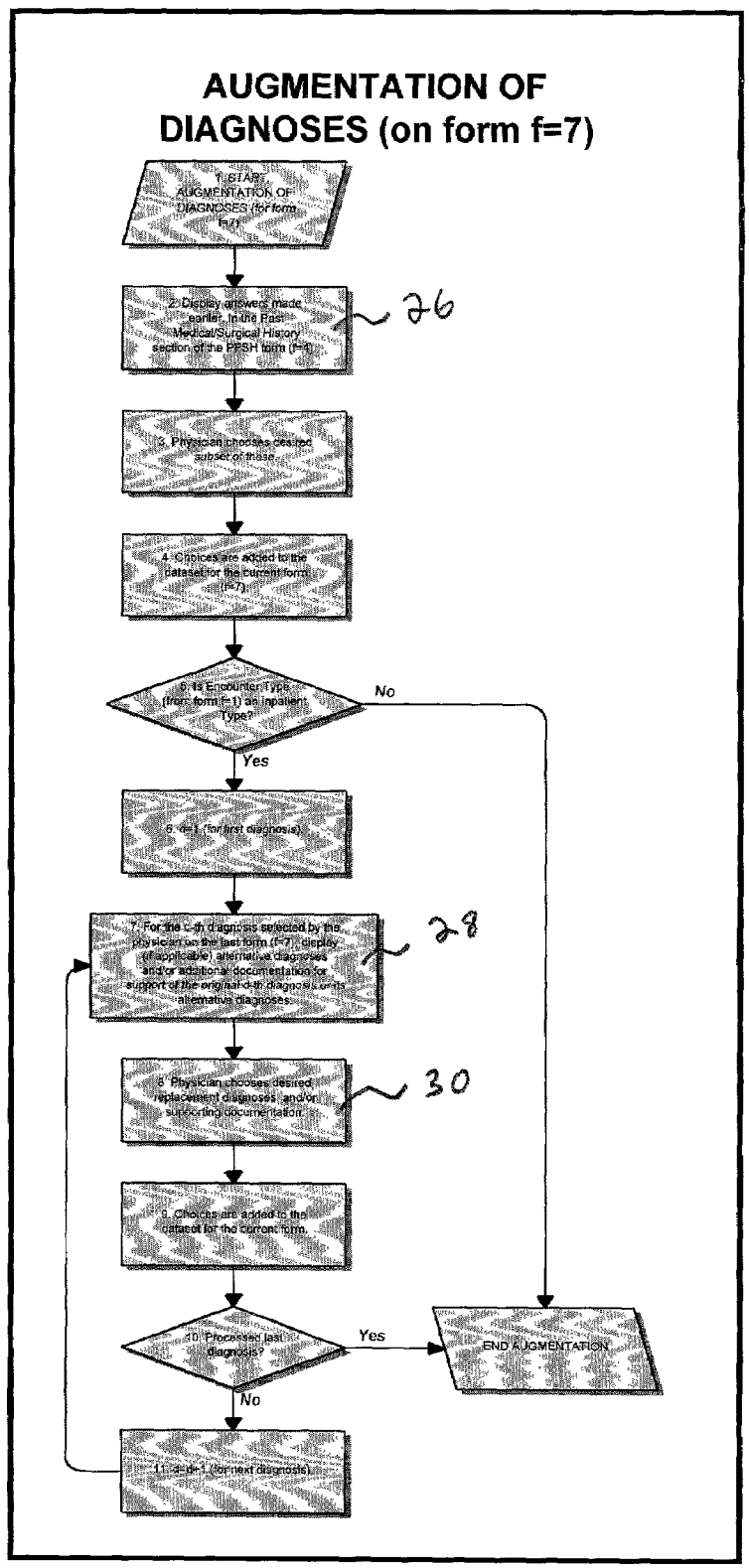
FIG. 2 is a flow chart diagram illustrating the preferred method of the present invention, particularly focusing on an augmenting feature of the present invention, the flow chart diagram specifically illustrating the use of the present invention with regard to a patient encounter with a health care provider.

The augmenting mechanism, as illustrated in FIG. 2, works by eliciting more accurate billing codes, diagnoses or documentation through the analysis of entered information (26) and predetermined criteria input. The augmenting mechanism is a selection option mechanism that provides the health care provider with alternative or additional diagnoses or documentation and suggests an appropriate billing code (28). The augmenting mechanism of the present invention also allows for the listing of all possible diagnoses for the entered information (28). Moreover, the augmenting mechanism reminds the health care provider of those diagnoses based on items such as laboratory results, radiological tests, diagnostic tests, and pathology reviews. The augmenting mechanism continuously assists the health care provider in completing these categories. Additional information not included in the forms is amenable and adapted to desired information (30).

The system of the present invention additionally provides for a checking mechanism that reviews and confirms the accuracy of previously entered information. The system reminds the health care provider of any lacking data needed to calculate the final medical billing code. Thus, as the health care provider completes a section, the system cues the health care provider to complete any remaining categories (28,30). Additionally, the system informs the health care provider about the number of categories that were completed versus the number of categories that could be completed to achieve the next E&M CPT-4 Code level. The system calculates the E&M CPT-4 code level according to requirements outlined in a table (FIG. 8). Therefore, the system suggests and encourages more complete documentation. (FIG. 1)

The recommendations for completeness are based on HCFA guidelines and are updated as HCFA rules change. The use of key word searches and drop down menus help improve completeness of diagnosis that comprise one part of the section in the Medical Decision Making component of the documentation system of the present invention. The key word search mechanism searches areas of the medical record and prompts the health care provider for information not contained in the medical record. Based on answers to the prompted questions, the system suggests appropriate details relative to specific diagnoses. These details help to more accurately describe the severity of illness of the patients and allow the Medical Coder to accurately code for these diagnoses. Drop-down menus are also utilized for suggestions of more appropriate diagnoses based on answers to the previously described prompts. This feature is specific for the inpatient medical records, allowing for more accurate assignment by the Medical Coder of the DRG.

The augmenting mechanism improves the accuracy of the medical coding and the overall quality of patient care by influencing the physician's decisions at the time of patient care delivery. Additionally, compliance with government regulations is increased and ensured. The augmenting mechanism significantly reduces the numbers of non-specific diagnostic codes. The Medical Coders have the details they need to assign a code with the required modifiers. The Medical Coders also use codes that more accurately reflect the severity of illness of the admitted patient. This is enabled though the augmenting mechanism that prompts the elicitation of additional information based on key word searches. These prompts are consistent with HCFA regulations that define the true illness level of the patient and the appropriate ICD code. The ICD-9 codes are the basis for the health care provider and facility (hospital) reimbursement. With accurate documentation and information, the augmenting mechanism assists the physician to generate codes that comply with government regulations and guidelines. The more documentation generally translates into better support of the inpatient record diagnoses and also translate into higher E&M CPT-4 and DRG Codes.

Some information prompting forms prompt the elicitation of information specifically needed by Medical Coders for the complete and accurate medical coding. The physician often does not realize the importance of including and documenting certain criteria. Types of information related to criteria include, but are not limited to, descriptions to complete the fourth and fifth digit modifiers for the ICD-9 (soon ICD-10) codes required for medical coding of the patient's file.

Additional features of the information prompting forms include, but are not limited to, prompts that recommend a specialty medical consultant. The system prompts the physician to order consultation in these cases. The use of consultation in particular cases has been shown to improve quality of care for the patient. The system also has drop-down menus with room for additional entry of documentation for the diagnosis. Free-text entry of a diagnosis is capable on the present invention. Additionally, the user is capable of viewing a list of diagnoses obtained from an outside source or program such as that found in "Alpha-II," which give all diagnoses and ICD-9 and CPT codes. Finally, a search engine working in conjunction with a listing of diagnoses is usable in triggering queries that aid in the augmenting mechanism of the present invention.

The augmenting mechanism provides the user with the option of tracking the percent of assigned E&M CPT-4 Codes in each level. The system is able to track the E&M CPT-4 Codes over a period of time to allow the physician to have a general idea of how many cases he has in each of the different E&M CPT-4 Code levels. The system also summarizes the E&M CPT-4 Codes assigned for each day of care for a particular patient. As a result, multiple reports for tracking trends of E&M CPT-4 Codes is possible as well as the E&M CPT-4 Code assignments for all the days for a particular patient. The codes for a particular patient is just as important for the physician as they are for the Medical Coder. The Medical Coders also correlate the E&M CPT-4 Codes with the facility codes.

After analyzing the general assessments, the augmenting mechanism searches key words to elicit more accurate and appropriate diagnoses. For example, a diagnosis of "urosepsis" triggers a query to the user. If, after prompting, the user checked off documentation consistent with "possible sepsis," then the software will prompt a diagnosis such as "urinary tract infection with possible sepsis" which, if more appropriate, is an alternative diagnosis. Therefore, the true level of illness and diagnosis of the patient is accurately provided. (FIG. 2) The software also prompts for completeness of documentation such as "the CBC demonstrates an elevated WBC" and "The patient's pulse was greater than 90." This information is added to the patient encounter documentation when approved by the Health Care Provider.

Figure 7:
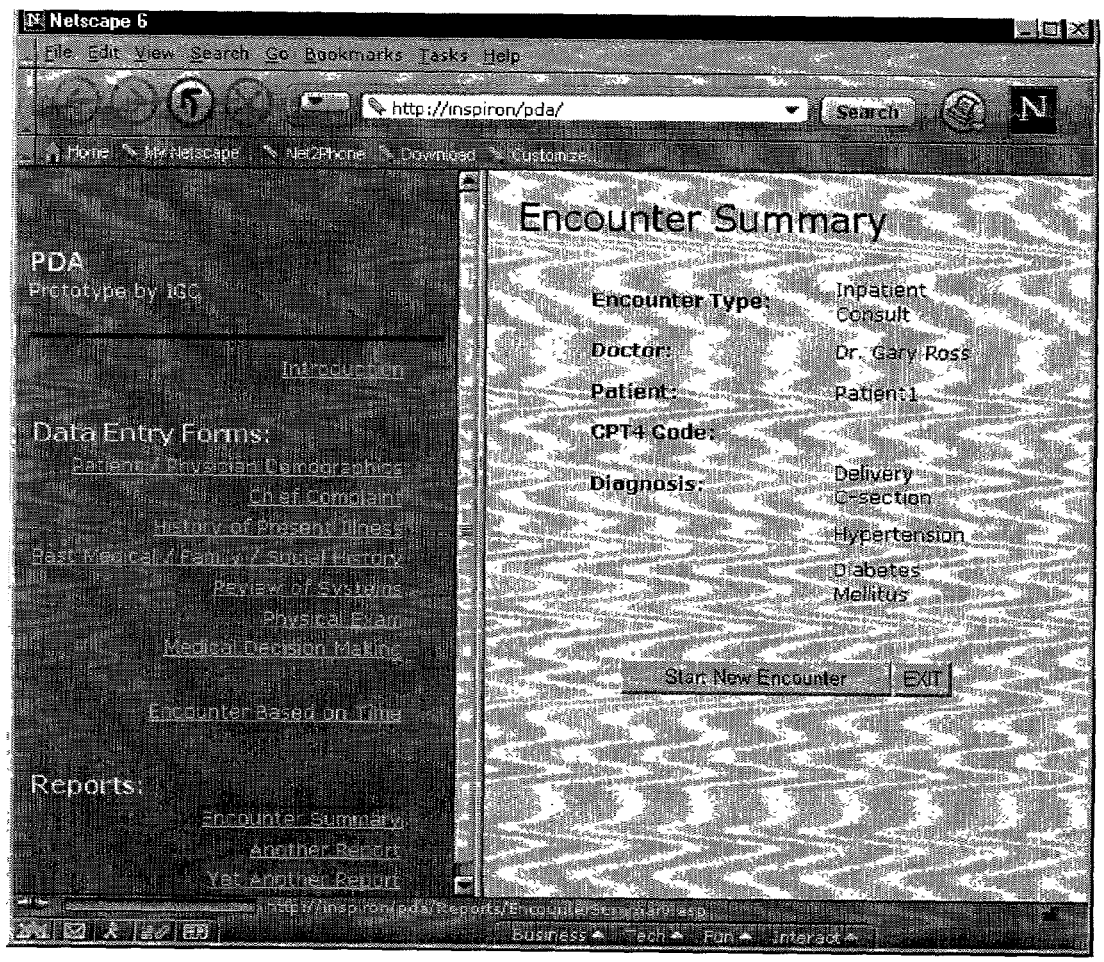
FIG. 7 is a view of one embodiment of the present invention on a web-based browser, this figure illustrating an example of a printable summary of the patient encounter with the health care provider, the summary form being dynamic and fully adaptable towards the user's preferences and needs.

After the documentation has been entered, the E&M CPT-4 Codes most appropriate for the entered documentation are calculated, generated and recommended for the health care provider (32). The system assigns the E&M CPT-4 Code based on an internal reference similar to the accompanying spreadsheet (FIG. 8). The documentation is electronically signed and electronically stored in the database. The user has the option of printing a hard copy for the medical record and electronically storing the copy. Additionally, a summary report is generated. (FIG. 7)

In utilizing the preferred embodiment, the health care provider fully and more accurately documents the patient encounter. The present invention is scalable for use on several patient encounters to be addressed by a single physician at the same time.

The preferred embodiment is compatible with technologies for electronic records, physician order entry, and technologies that are reservoirs for other aspects of the medical record. The documentation software of the preferred embodiment is able to link with the information created by the registration software. The software also links to the billing department and corresponding software. Indications for procedures and procedure documentation are entered via templates that have prompts for addressing the specific details for the individual patient. Report writing capabilities include, but are not limited to, E&M code summaries for each physician, E&M code summaries for each day of care for Inpatient Medical Coders, data extraction by particular key word responses and answers, data extraction to capture all Physician code overrides, data extraction to capture all user free text entries, customized reports, and any other relevant information that would aid the health care provider.

There is the ability for key word searches for specific historic facts, physical findings or diagnoses. These searches help in identifying trends in diagnoses or which cases had certain findings for research purposes.

The present invention is flexible enough to be used in multiple situations, interfacing with general ADT software. It works in conjunction with, bar coding and touch screen technology, wireless technology, central data warehousing, and multiple data entry devices. This dramatically improves the quality of the physician portion of the medical record as well as the accuracy of representation of severity of illness of the patient both in the documentation and for the Medical Coder. This is true for E&M CPT-4 Codes as well as for inpatient DRG coding. The present invention also helps documentation with the use of APGs and APCs.

There is capability to offer compliance checking for physicians not using the present invention. The pertinent elements of the encounter are inputted into the template to determine if elements are missing and to determine the appropriate code. The feasibility exists to use the present invention for this purpose alone either as a freestanding tool or in conjunction with consulting services. This works via a Web based input document as well. Additionally, the present invention aids case managers in proving the need for continued in-hospital stay to HMO officials and other third party payers in order to obtain authorizations. The prompts also assist in tracking documentation for specific treatment initiatives. For example, the recommendation of smoking cessation interventions after the software identifies the patient as a smoker. Finally, the present invention is capable of identifying patients that fit discharge criteria to shorten the average length of stay for certain diagnoses that have well defined criteria.

In operation, the preferred method of documentation for accurately and completely determining payment reimbursement comprises the steps of prompting the elicitation of information relevant to the determination of the appropriate payment codes; entering and storing the prompted information; analyzing the prompted information; and converting the analyzed information into payment codes based upon various predetermined criteria.

EXAMPLES

Example One

A preferred embodiment of the present invention, as generally shown in FIG. 1, is operated in a medical field setting wherein a patient and health care provider interact with each other (10). All users of the documentation system first must log into the system by providing a user name and password in order to gain access to all confidential patient informational files (12). Once access to the documentation system is allowed, the user will be shown a main menu page (12) wherein the user selects the patient file to be accessed or enter new patient information. Each patient file contains different information prompting forms (14) from which the user then selects to view. The user selects the desired form (16) through drop down menus or links viewed on the main menu page. (FIG. 3) If the user desires to utilize the auto completion function utilizing the present invention's data entry mechanism, then the user simply types in abbreviated or complete terms to be searched.

After selecting the desired patient file or entering the new patient information, the user accesses the site of care screen. The site of care screen is set as a default screen or is accessed through the main screen menu page. The user then provides the site of care in which the patient is currently being examined. For instance, the site of care includes the emergency room, hospital, extended care facility or medical office. Once the site of care information is provided, the user selects the next information prompting form (20) that provides queries to the user for entering patient data. The forms include, but are not limited to forms for eliciting information regarding demographics, chief complaints (FIG. 4), history of present illness, past medical family social history, review of systems, and physical exam. The queries presented on each form have predetermined answers or allow for free-text entry of answers appropriate to each presented query.

The user then enters the type of information prompting form being entered, for example the user selects the consult form and then the Chief Complaint form (FIG. 4) by any methods of data entry depending on the hardware being used. Additionally, there are drop-down menus for key terms or items for chief complaints as well.

The user accesses another general category entitled, "History of Present Illness" that prompts for common descriptions such as timing, duration, context, quality, severity, location, modifying factors, and associated signs and symptoms The user also accesses the Review of Systems form that includes the general review of systems as outlined by HCFA and has drop down menus for each category. Finally, the user has access to the Past Family Social History form and Physical Examination form.

If documentation was skipped from any of these categories the computer cues the user to remind the individual that those categories were not completed (22). The computer informs the user about the number of categories that were completed versus the number of categories that could be completed to achieve the next E&M CPT-4 Code level, thus encouraging more complete documentation. The levels of service are provided by "time" appropriate cues. For example, time of "service for counseling" or "coordination of care" when greater than fifty percent of the total time spent for that patient would allow entry into this category. Entry of the general counseling topics summarizes the coordination of care and documents the counseling thereof. The user is prompted to make sure this part of the form is completed appropriately. (See generally, FIG. 1)

The user finally accesses the Medical Decision Making section and form (FIG. 2) listing all the diagnoses. There are reminders including those diagnoses based on items such as laboratory results, radiological tests, diagnostic tests, and pathology reviews. Under the Risk section of Medical Decision Making, drop down menu assist the physician in completing these categories. Under the Data section of the Medical Decision Making, drop down menus assist the physician in completing this category. Additional information not included in the menus is amenable and adapted to desired information.

The Physical Exam section follows the general categories as outlined by HCFA and has drop down menus for the common physical findings for each of the major categories such as in the constitutional, eyes, ears, nose, mouths and throat categories.

After analyzing the general assessments, the system searches key words to elicit more accurate and appropriate diagnoses. For example, a diagnosis of "urosepsis" triggers a query to the user. If, after prompting, the user checked off documentation consistent with "possible sepsis," then the software will prompt a diagnosis such as "urinary tract infection with possible sepsis" which, if more appropriate, is an alternative diagnosis. Therefore, the true level of illness and diagnosis of the patient is accurately provided. (FIG. 2) The software also prompts for completeness of documentation such as "the CBC demonstrates an elevated WBC" and "The patient's pulse was greater than 90." This information is added to the patient encounter documentation when approved by the Health Care Provider.

When the patient encounter and documentation are completed, the system calculates and generates a recommended E&M CPT-4 Code (32). The documentation is electronically signed and electronically stored in the database. Finally, a hard copy of the documentation and summary thereof is printed (FIG. 7).

Example Two

The preferred embodiment of the present invention is implemented as a database-connected web application that runs on a Microsoft webserver ("server") such as Internet Information Server ("IIS") or Personal Webserver ("PWS"). In this embodiment the user views, and interacts with, the application using a standard web browser, such as Microsoft Internet Explorer or Netscape Navigator ("client").

The preferred embodiment of the present invention employs various technologies including Microsoft Active Server Pages ("ASP"), which use ASP code to allow the application to carry out logical processing on the server ("server-side"). The web pages are all ASP pages (*.asp files), which also incorporate Hypertext Markup Language ("HTML") code to control the web page layout and is run on the client. Additionally, the pages incorporate VBScript, a scripting language used in conjunction with ASP to allow the application to carry out server-side processing and Javascript, a scripting language used to allow the application to carry out logical processing on the client ("client-side processing") and Q Microsoft Access Database. This is a relational database, which the invention uses to store the data that it needs as input to perform its calculations as well as to store the data that it outputs to record the doctors' encounters with the patients.

The above implementation is only one of many that could have been used. For example, the Access database could easily be substituted by any other relational database, such as Oracle or SQL Server. ASP is a Microsoft technology to allow web pages to execute programs on a web server. To execute such programs from a web page on a non-Microsoft web server, such as a Unix-based or Macintosh-based web server, Java Server Pages ("JSP") technology could be used in place of ASP.

Similarly, other alternatives to Microsoft's ASP for writing server-side programs for web pages that run on essentially an arbitrary platform, are, PHP (publicly available), CGI (Common Gateway Interface) scripts written in Perl, Python, etc., and CFML/Macromedia's Cold Fusion.

The above technologies are for developing web applications (applications served by a web server and viewed by the user via a web browser client). Alternatively, the invention could readily be written as a stand-alone desktop application, rather than as a web application, using such languages as Basic, C, C++ or Pascal, in version suitable for the desired target platform e.g. Microsoft Visual Basic for Microsoft computers etc, or in Sun's Java language, which creates effectively platform independent code.

Throughout this application, various publications, including United States patents, are referenced by author and year and by patent number. Full citations for the publications are listed below. The disclosures of these publications and patents in their entireties are hereby incorporated by reference into this application in order to describe more fully the state of the art to which this invention pertains.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A clinician documentation method for use with an electronic processing device to better support and define a medical diagnosis as needed for appropriate DRG (Diagnosis Related Group) assignment comprising the steps of:

navigating through an information prompting form relevant to a patient encounter and inputting patient data therein;

displaying previously entered information and corresponding conclusions;

selecting the desired information and corresponding conclusions to be augmented;

providing at least one of alternative conclusions and criteria not previously input to be inputted;

choosing at least one of the previously entered information, corresponding conclusions, alternative conclusions, and criteria not previously input;

calculating accurate conclusions based upon all entered information and related predetermined criteria;

repeating said navigating, displaying, selecting, providing, choosing, and calculating steps for at least a second information prompting form;

recording and saving the calculated conclusions;

summarizing all entered data; and providing an appropriate DRG assignment for the patient.

* * * * *